US010383669B2

(12) United States Patent
Graham

(10) Patent No.: US 10,383,669 B2
(45) Date of Patent: Aug. 20, 2019

(54) INTERPHALANGEAL JOINT IMPLANT METHODS

(71) Applicant: Michael Graham, Machomb, MI (US)

(72) Inventor: Michael Graham, Machomb, MI (US)

(*) Notice: Subject to any disclaimer, the term of this patent is extended or adjusted under 35 U.S.C. 154(b) by 0 days.

(21) Appl. No.: 14/321,626

(22) Filed: Jul. 1, 2014

(65) Prior Publication Data
US 2014/0316474 A1 Oct. 23, 2014

Related U.S. Application Data

(62) Division of application No. 13/484,861, filed on May 31, 2012, now Pat. No. 8,764,842.

(51) Int. Cl.
A61B 17/84 (2006.01)
A61F 2/42 (2006.01)
A61B 17/72 (2006.01)
A61B 17/68 (2006.01)
A61F 2/30 (2006.01)

(52) U.S. Cl.
CPC ........... *A61B 17/846* (2013.01); *A61B 17/68* (2013.01); *A61B 17/7291* (2013.01); *A61F 2/4225* (2013.01); *A61F 2/4241* (2013.01); A61F 2002/30622 (2013.01); A61F 2002/4228 (2013.01); A61F 2002/4233 (2013.01); A61F 2002/4243 (2013.01); A61F 2002/4246 (2013.01); A61F 2002/4248 (2013.01)

(58) Field of Classification Search
CPC ........... A61F 2002/4243; A61F 2/4225; A61F 2002/4248; A61F 2002/4228; A61F 2002/30622; A61B 17/7291; A61B 17/7258; A61B 17/7266; A61B 17/846

USPC ................. 623/21.15, 21.19, 23.39
See application file for complete search history.

(56) References Cited

U.S. PATENT DOCUMENTS

| 5,417,692 A * | 5/1995 | Goble | A61B 17/68 433/173 |
| 5,643,267 A * | 7/1997 | Hitomi | A61B 17/72 24/694 |
| 8,303,666 B2 * | 11/2012 | Vanasse | A61F 2/42 623/21.11 |
| 2010/0036439 A1 * | 2/2010 | Lavi | A61B 17/7225 606/308 |

(Continued)

FOREIGN PATENT DOCUMENTS

WO    WO 2012055999 A1 *  5/2012 ............... A61F 2/42

Primary Examiner — David H Willse
Assistant Examiner — Javier G Blanco
(74) Attorney, Agent, or Firm — Houtteman Law LLC; Scott Houtteman

(57) ABSTRACT

A method and apparatus for correcting malformed joints, in particular the "hammer toe" contraction of the proximal interphalangeal joint. The disclosure comprises a two-component implant: a proximal phalanx component and a middle phalanx component. An endosseous stem on each component is inserted axially into the end of a respective host bone and, after insertion, the components are attached. The attached components are held together in various ways, for example a detent arm/aperture mechanism. Each component can be cannulated to allow for the passage of a kirschner wire, if necessary, to stabilize adjacent joints such as the proximal interphalangeal joint. The bones of the treated joint can be set to form a desired angle by adjusting the angle formed by the corresponding endosseous stems.

6 Claims, 7 Drawing Sheets

(56) References Cited

U.S. PATENT DOCUMENTS

2011/0004255 A1* 1/2011 Weiner et al. ................ 606/301

* cited by examiner

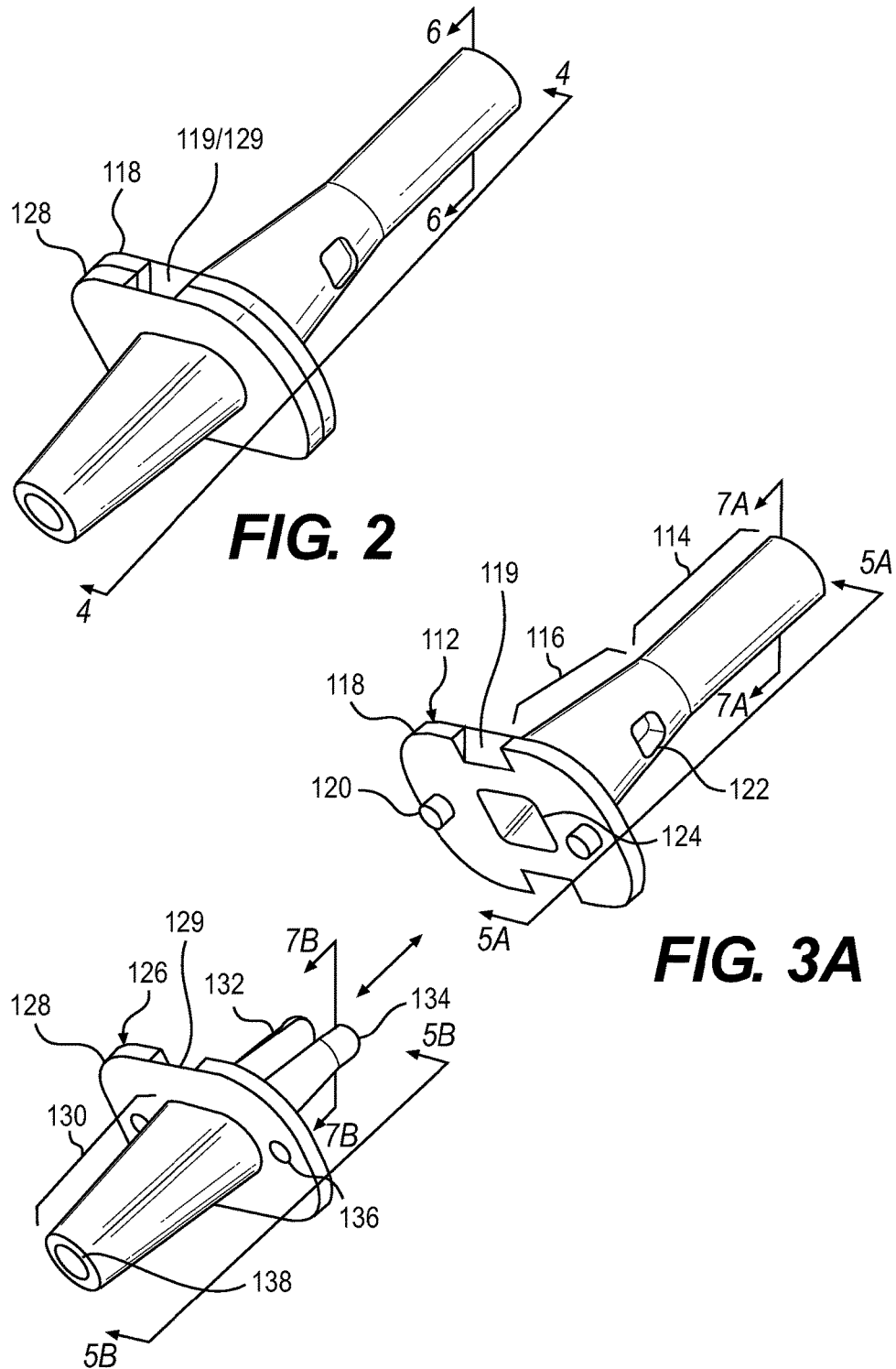

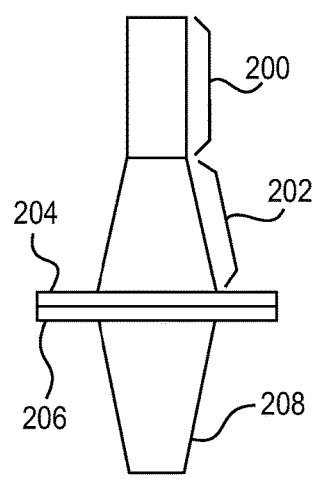
FIG. 8
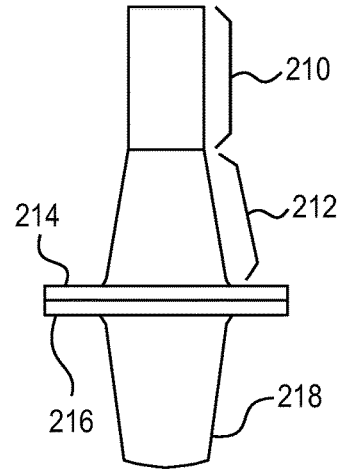
FIG. 10
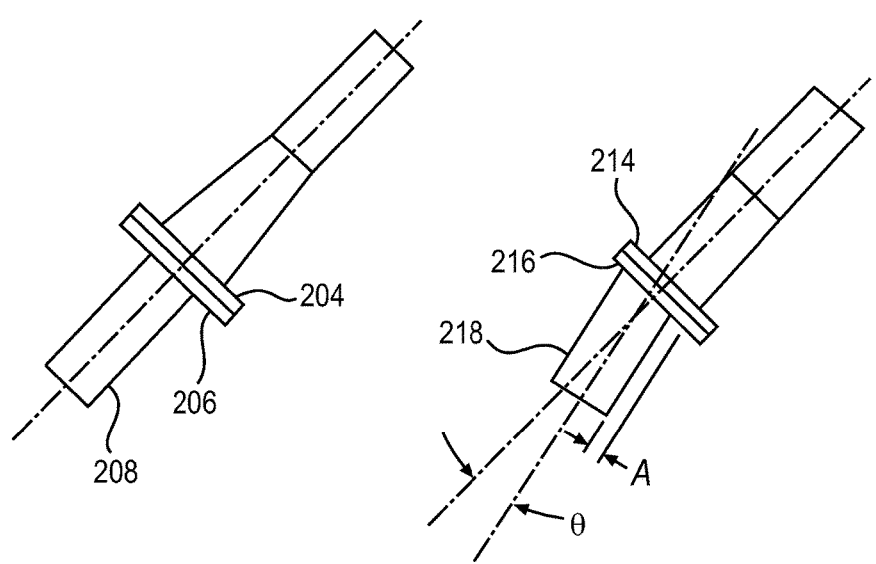
FIG. 9   FIG. 11

INTERPHALANGEAL JOINT IMPLANT METHODS

This application is a Divisional of U.S. application Ser. No. 13/484,861, filed May 31, 2012, now U.S. Pat. No. 8,764,842.

BACKGROUND OF THE INVENTION

This disclosure relates to a method and apparatus for correcting abnormal flexion of the joints of the human foot. More particularly, this disclosure relates to a combination of dorsifexion of the metatarsal/proximal phalangeal joint and plantar flexion of the proximal interphalangeal joint, commonly called a hammer toe.

The lesser toes of the human foot are composed of three bones and contain two joints. The three toe bones are a proximal phalanx (closest to the metatarsal bone), a middle phalanx, and a distal phalanx (at the end of the toe). The three toe bones are connected by two toe joints, a proximal interphalangeal joint (PIPJ), which is formed by a distal end of the proximal phalanx and a proximal portion of the middle phalanx; and a distal interphalangeal joint (DIPJ), distal to the PIPJ and formed by a distal end of the middle phalanx and a proximal end of the distal phalanx.

Contraction of the lesser toes of the foot is a common pathologic condition due to an imbalance between the tendons on the top and bottom of the toe(s). When an affected toe is able to be straightened out manually, i.e. by an individual or an eternal force, it is referred to as a flexible hammer toe. If left untreated these flexible contractures will become a fixed deformity know as a rigid hammer toe, which cannot be put back into normal alignment. The PIPJ is more implicated in a hammer toe syndrome deformity then the DIPJ.

There are many palliative modalities such as pads and various forms of orthodigital devices used to accommodate toe deformities. Those conservative options, however, do not provide an individual with enough comfort and in some cases are simply illogical given the fact that various alternative surgical options are available.

Throughout the history of performing toe surgery many methods have been attempted by surgeons ranging from simple tendon release, partial joint excision, full joint excision and, as a final resort, complete fusion (arthrodesis) of a joint rendering a straight toe. Arthrodesis of the joint is usually reserved for severe deformities or in cases where previous non-arthrodesic procedures were performed but failed to provide a patient with desired expectations.

In the past some surgeons fused the PIPJ joint by a simple end-to-end method. In this procedure a surgeon resects the articular cartilage of the end of one toe bone and the base of an adjoining bone which forms an abnormal joint. The two ends are approximated to each other with the expectation that they will fuse together. An inherent problem with this method is a high rate of non-union with possible recurrence of deformity.

Another method is to insert a smooth pin or wire that extends out of the distal end of the toe. The wire is used to hold the ends of the bones in alignment until fusion occurs. Because these wires and pins are smooth, however, it is possible for the joint to distract leading to a failure or non-union.

Additionally, yet another method was developed which utilized a thin screw inserted from the tip of a toe across the joint. The purpose of this device was to provide compression which facilitates end-to-end fusion. The insertion of a specialized screw is difficult to perform and presents a possibility of damaging the DIPJ. Furthermore, when the pin is removed it requires a second surgical procedure.

Yet, another device was developed utilizing "memory" metal that was simply inserted into either the DIPJ or PIPJ after resection of the joint. These devices are relatively expensive when compared to pins, wires, or screws and also have been known to sometimes expand too quickly rending the device ineffective.

Finally, a hinged toe fusion device was developed to replace the PIPJ. Each end of the device was inserted into a corresponding end of the bones flanking the PIPJ. A limitation with this device is that it is relatively difficult to work with. The two components are not designed to be easily separated. Also, the device can be difficult to properly align and can rotate out of the proper position after insertion. Also, it does not allow for the additional use of a pin or wire to be inserted across the metatarsophalangeal joint (MPJ), the joint proximal to the PIPJ, which is sometimes desirable.

The difficulties and limitations suggested in the preceding are not intended to be exhaustive, but rather are among many which demonstrate that although significant attention has been devoted to surgically correcting hammer toe disfigurement, nevertheless surgical implants and procedures appearing in the past will admit to worthwhile improvement.

BRIEF SUMMARY OF PREFERRED EMBODIMENTS

The subject disclosure includes advantages of bone fusion while simplifying the procedure and decreasing or eliminating incidences of non-union and non-alignment. A preferred embodiment comprises a two-component device including (1) a proximal phalanx component and (2) a middle phalanx component. The two components are handled separately during a surgical procedure. Each is inserted axially into a respective host bone. After insertion, the components are joined. The attached components are held together in various ways, for example a detent arm/aperture mechanism. As the components are brought together, the arms of one component slide into a central channel, or cannula, in the other component. The arms are spring loaded as they first encounter an inner surface of the cannula and then spring out when the arms encounter lateral apertures present further on along the cannula. Each component can be cannulated to allow for the passage of a wire, e.g. 0.045 inch kirschner wire (k-wire), which passes through the center to stabilize either the DIPJ or the MPJ.

An interphalangeal joint implant is inserted using the following procedure. A surgeon exposes the PIPJ, separates the two bones making up the joint and then removes the articular cartilage. Next, a device, such as a trephine, is used to "core" the ends of the bones on each side of the joint. The trephine removes a central cylindrical section of bone within the bone shafts which allows for a press-fit junction of the stems of the opposing implant components. A stem of the proximal implant component is inserted into the proximal phalanx and a stem of a distal implant component is inserted into the middle phalanx. These endosseous stems preferably are non-cylindrical in shape. This will inhibit unintended rotation of the implant after insertion. If stabilization of an adjacent joint is required a k-wire can be directed from within the joint out through the tip of the toe making certain that the proximal end of the wire will not prevent the fastening together of the two implant components. The middle phalanx portion would then be fitted to the proximal phalanx portion and then the k-wire can be passed through the MPJ.

THE DRAWINGS

Numerous advantages of the present disclosure will become apparent from the following detailed description of preferred embodiments taken in conjunction with the accompanying drawings wherein:

FIG. 2 is an axonometric view of an interphalangeal joint implant in accordance with a preferred embodiment of the invention;

FIGS. 3A-3B are axonometric views of individual proximal and distal components of the interphalangeal joint implant depicted in FIG. 2;

FIG. 8 is a top view of the interphalangeal implant shown in FIG. 2;

FIG. 9 is a side view of the interphalangeal implant depicted in FIG. 8.

FIG. 10 is a top view of an alternative preferred embodiment of the interphalangeal implant;

Figure 12A:
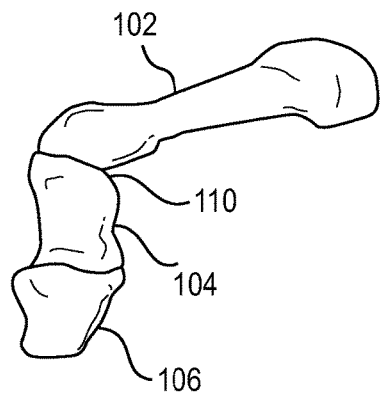
Figure 12B:
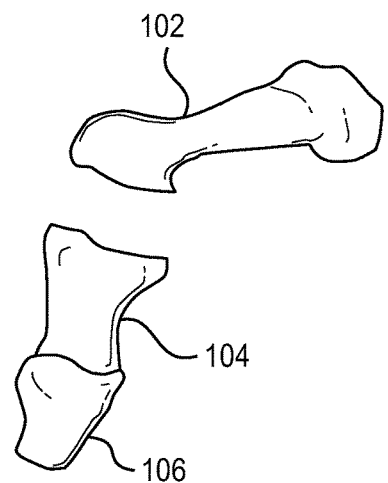
Figure 12C:
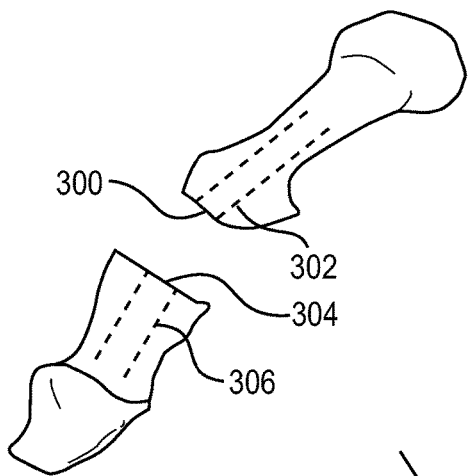
Figure 12D:
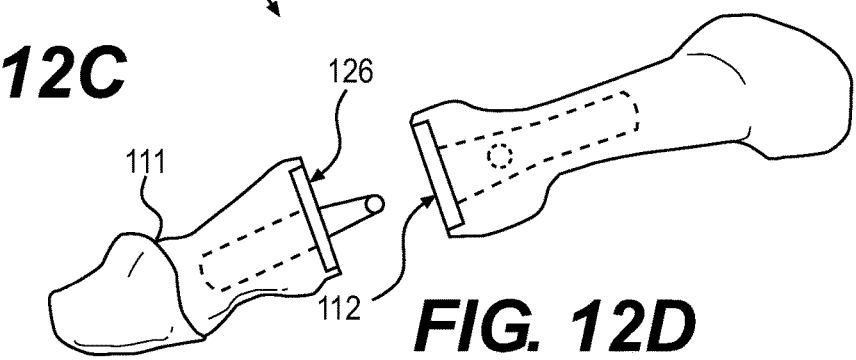
Figure 12E:
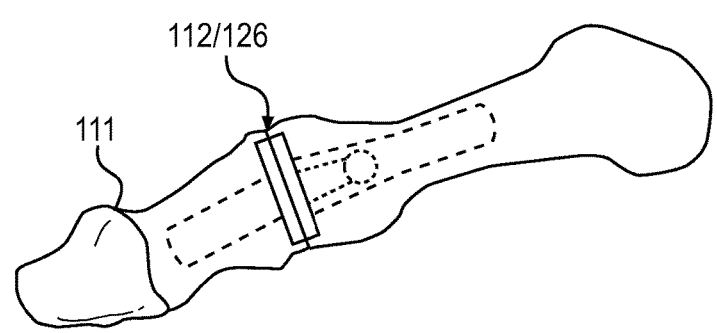

FIG. 11 is a side view of the interphalangeal implant depicted in FIG. 10 illustrating one of the endosseous stems with an imaginary central longitudinal axis offset from the other stem's axis by a distance "A," and by an angle Theta (θ); and FIGS. 12A-E illustrate, in schematic format, a procedure for correcting a misaligned PIPJ (FIG. 12A) where the bones flanking the PIPJ are separated (FIG. 12B), tissue around the PIPJ is removed (FIG. 12C), the implant components are inserted, one into each of the bones flanking the PIPJ (FIG. 12D), and the components of the implant are joined into an integrated unit (FIG. 12E).

DETAILED DESCRIPTION

Context of the Invention

Figure 1:
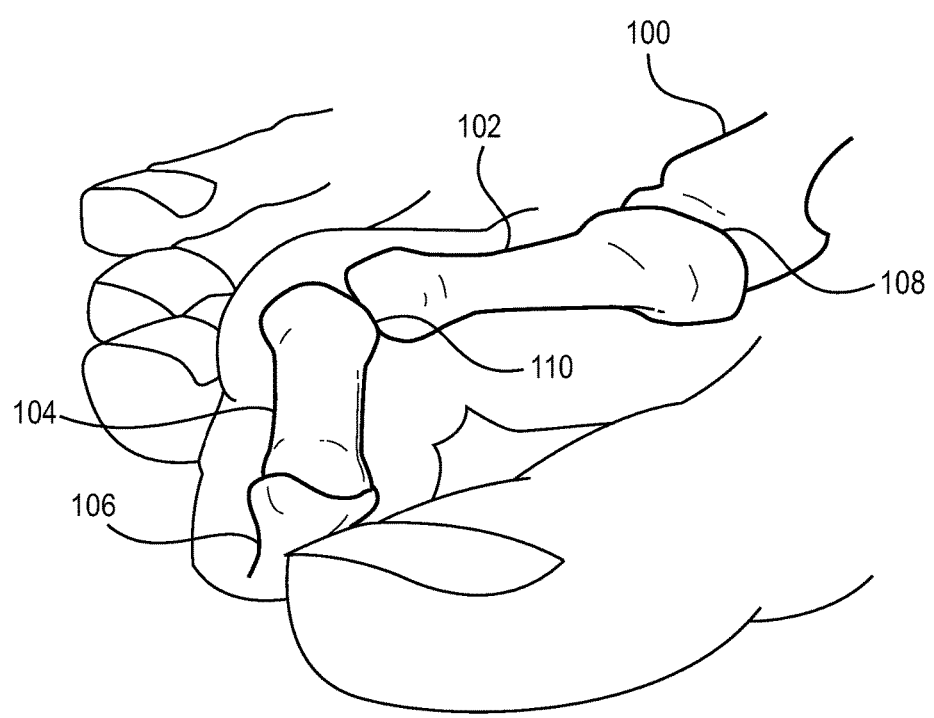
FIG. 1 is an axonometric view of a context of the disclosure comprising a front portion of a human foot with some flesh removed from a lesser second toe to illustrate severe plantar flexion of the proximal interphalangeal joint ("PIPJ") reflecting a rigid joint deformity commonly known as hammer toe.

Referring now particularly to the drawings, wherein like reference characters refer to like parts, and initially to FIG. 1, there will be seen a schematic illustration of a context of the subject disclosure—a misaligned interphalangeal joint commonly referred to as a "Hammer toe."

The disclosure is directed to correction of misalignment between virtually any two bones, but particularly for the flange bones that make up the five digits of the foot and hands. A typical bone misalignment is illustrated in FIG. 1, with flesh removed from a second toe for illustrative purposes. Depicted are a metatarsal 100, proximal phalanx 102, middle phalanx 104 and distal phalanx 106 bone segments in a human foot. As noted above, FIG. 1 illustrates a hammer toe condition characterized by dorsifexion of the metatarsal/proximal phalangeal joint 108 and plantar flexion the proximal interphalangeal joint ("PIPJ") 110. The subject apparatus and procedure are directed to correction of this abnormal flexion of the PIPJ. Although the subject disclosure is directed in particular to medically correcting hammer toe syndrome it is also useful for more curved or claw toe maladies as well. In this sense the term hammer toe as used herein includes claw toe, mallet toe and curly toe conditions. The disclosure also applies to analogous conditions affecting human fingers.

Interphalangeal Joint Implant

FIG. 2 illustrates an axonometric view of the device with two component parts operably joined together. FIG. 3A is the proximal phalanx component and FIG. 3B is the middle phalanx component of a human second toe.

The proximal phalanx component 112, FIG. 3A, is designed to be inserted into the distal end of the proximal phalanx. It comprises an endosseous stem 114, 116 and a base 118. The stem is either cylindrical, non-cylindrical or a combination of the two. A non-cylindrical shape has the advantage that the stem will not easily rotate after insertion into the proximal phalanx. The component 112 illustrated in FIG. 3A combines a cylindrical portion 114 at the tip of the stem and a non-cylindrical, oval or regular trapezoidal portion 116 at the base of the stem. The shape need not be oval or regular trapezoidal. Any shape that is non-spherical in cross-section will function to inhibit rotation of the device once it is inserted into the bone. Other measures can be employed to inhibit or prevent rotation such as the use of adhesives or surgical cement. Also, the device can be designed to screw into place provided one insures that the device will be in the proper orientation when the base of the device contacts the end of the bone.

Other structures can be added to the device to inhibit an untended tendency for the device to loosen or slide out from the end of bone. For example, the device can have regular or irregular surface protrusions. Alternatively, the surface of the stem can have various structures and shapes that promote tissue in growth such as interstitial spaces, ribs, channels, holes, grooves and the like.

The proximal phalanx component 126 also contains a base 128. When the component is fully inserted, the base will be flush against the distal end of the proximal phalanx, in position to contact the corresponding base of the middle phalanx component illustrated in FIG. 3B.

The base can be equipped with a registry structure that will insure the bases, FIG. 3A and FIG. 3B, will properly align when brought into contact. A preferred registry structure is illustrated in FIG. 3A, two pins 120 that interact with correspondingly shaped circular cavities 136 in the base 128 of the middle phalanx component illustrated in FIG. 3B.

The middle phalanx component, FIG. 3B, designed for insertion into the proximal end of the middle phalanx, will be generally smaller than the proximal phalanx component of FIG. 3A but is similar in other respects. The middle phalanx component will have an endosseous stem 130 and a base 128. The stem can be either cylindrical, non-cylindrical or a combination of the two, just as its counterpart in FIG. 3A. The stem illustrated in FIG. 3B has a non-cylindrical, oval shape 130.

The middle phalanx component, like its proximal phalanx counterpart, can have additional structures that inhibit (or prevent) the device from rotating or otherwise loosening after it is inserted into the end of the bone.

Figure 4:
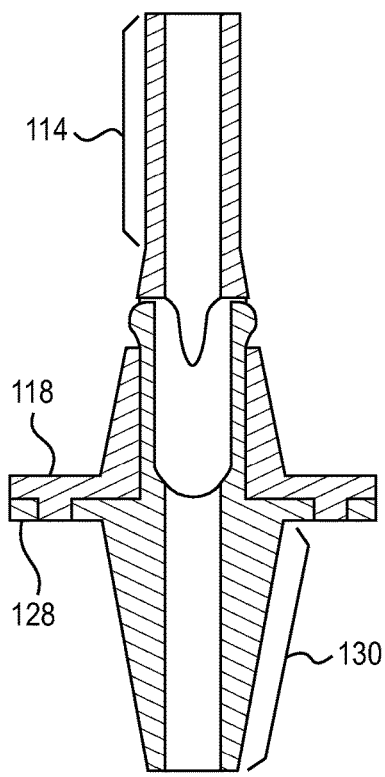
FIG. 4 is a cross-sectional view taken along section line 4-4 of FIG. 2.
Figure 5A:
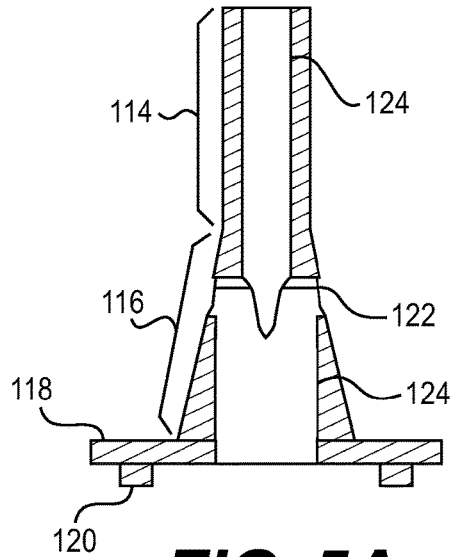
FIGS. 5A-5B are cross-sectional views taken along sections line 5A-5A and 5B-5B in FIGS. 3A and 3B, respectively.
Figure 5B:
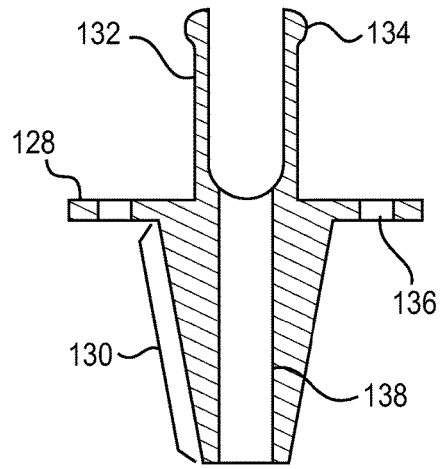

When the two components are brought together in correct alignment, a locking mechanism will engage and hold the components together. A preferred locking mechanism features lateral detent arms on one component and a corresponding aperture on the other component. As the two components are slid together the arms are spring loaded then, when they encounter apertures on the corresponding component, the arms spring out and lock the two components together. An example of this preferred locking mechanism is seen in FIGS. 4, 5A and 5B, which are cross-sections of FIGS. 2, 3A and 3B respectively. FIG. 5B illustrates detent arms 132 which have a bulge at the head 134. The arms are designed so that they can be compressed into an opening 122 (FIG. 3A) in the complementary component. Then the arms will spring out when the bulge 134 lines up with the mating aperture 122 in the complementary component. The two components locked together can be seen in FIG. 2 and FIG. 4 which is a cross-section of FIG. 2 taken along line 4.

Figure 6:
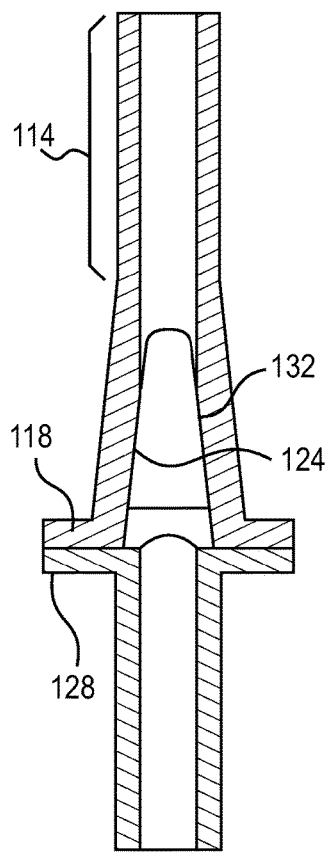
FIG. 6 is a cross-sectional view taken along section line 6-6 in FIG. 2.
Figure 7A:
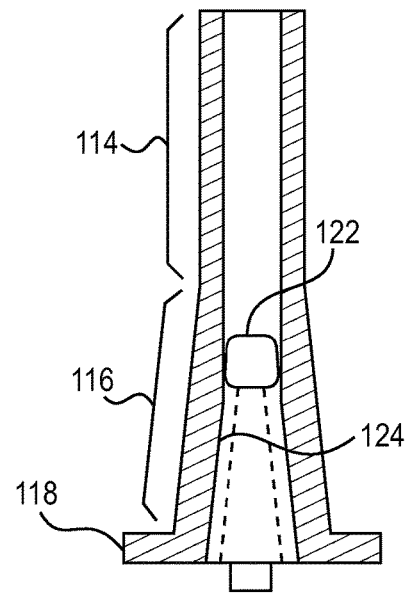
FIGS. 7A-7B are a side views taken along section lines 7A-7A and 7B-7B in FIGS. 3A and 3B, respectively.
Figure 7B:
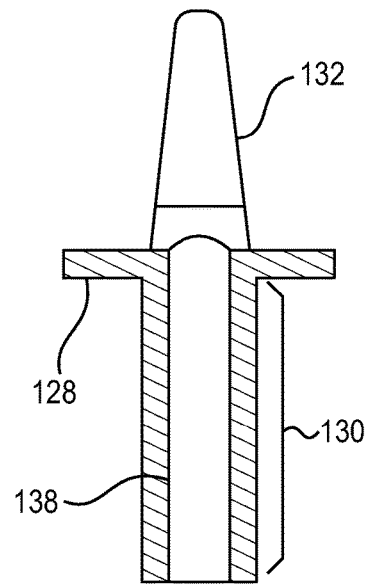

The locking mechanism can have an additional design function which allows the two components to properly align and maintain a proper alignment. This is illustrated in FIGS. 6, 7A and 7B, which are cross-sections of FIGS. 2, 3A and 3B taken along line 6, 7*a* and 7B, respectively. The arms have a taper 132 as shown in FIG. 7B that is sized to completely fill a complementary taper on said parallel inner surfaces 124 shown in FIG. 7A. The taper insures proper alignment and prevents rotation of the components after the components are locked together as shown in FIG. 6.

Other structures and mechanical components in addition to the one illustrated here can perform the function of locking the two components together. These can be differently shaped prongs, flexible links or any other type of arm or protrusion that extends from one component to the other. The structures can be any male/female pair of mating structure that, when the pairs contact each other, lock the two components together.

Alternatively, the structure used to lock the components together can be extra elements such as various epoxies, adhesives, magnets or the addition of a third structure specifically designed for locking, such as a clip. This third structure would be moved into position and interact with structures on both pieces and keep them together. Of course any common locking mechanism will function with this device such as screws, pins, rivets, nuts and bolts and the like. A preferred locking structure is a detent arm/aperture mechanism.

Under certain conditions it may become desirable to remove the implant or merely separate the two components after they have been joined. For this purpose a separation notch 119/129 is provided as shown in FIG. 2. The notch is shown in the separated components 119, 129 in FIGS. 3A and 3B. The surgeon can insert into the notch a surgical tool that creates leverage and mechanical advantage allowing the surgeon to pry apart the two components.

The purpose of the implants is to treat bones in an abnormal and sometimes dysfunctional position, such as a hammer toe, and to reestablish function. The bones must function properly throughout active motion of the foot as well as when the foot is at rest. To a first approximation, the functional position is to straighten the PIPJ joint, that is, the longitudinal axis of the proximal phalanx is in axial alignment with the longitudinal axis of the middle phalanx. This may not, in practice, be the optimal position for the PIPJ joint. In another preferred embodiment, a slight angle between these bones may be more functional for a patient. In this case the implants can be altered so that the PIPJ varies from straight to 15° from linear. A preferable angle is 10° from linear. These embodiments are illustrated in FIGS. 8 through 11. FIGS. 8 and 9 illustrate a device designed to produce a perfectly straight (0° angle) PIPJ joint. FIG. 8 is a top view of the device. FIG. 9 is a side view. Compare these to FIGS. 10 and 11, which illustrate a device in which the PIPJ joint will be offset from perfectly straight by the angle "θ" which, in this example, is 10°. FIG. 10 is a top view and FIG. 11 is a side view.

Notice that the middle phalanx component 218 in FIG. 11 is offset from the proximal phalanx component 210, 212 by a distance of "A." This offset is provided to deal with an issue arising from cannulation of the device. When the device is straight, that is, designed to generate a 0° angle for the PIPJ joint, a cannulation will pass straight down the central axis of both components of the device. The cannulation will enter at the proximal end of the proximal phalanx component and exit out the distal end of the middle phalanx component. When, however, the device is angled a cannulation entering at the proximal end of the proximal phalanx component may exit out the side of the middle phalanx component, rather than the end.

This problem is resolved as shown in FIG. 11. An offset will allow the cannulation to continue straight through the middle phalanx component and exit out the end. In FIG. 11 the central longitudinal axis of the proximal phalanx component is shown. Note that this axis is extended down the length of the middle phalanx component 218 and exits through the end of the middle phalanx component. This is because the middle phalanx component is offset dorsally (in FIG. 11 this is to the left) by the distance "A." If the middle phalanx component were not dorsally offset, the central axis line would exit on the dorsal (left) side of the middle phalanx component rather than out the end, as shown. Thus, this offset allows a straight cannulation to pass from one end of the two component device to the other, even if the central axes of the two components are not collinear.

While a preferred embodiment of the device is use in the PIPJ to correct hammer toe, the device is not limited solely to use with the lesser toes but can also be used in fingers as well as the thumb and great toe. Indeed, variations of the device can treat a wide variety of maladies related to improper bone alignment. A non-exhaustive list of examples includes: flexible and rigid hammer toe, deviated/crooked toes or fingers (caused by either physical injury or inherited) arthritic joints, claw toe, mallet toe and long toes requiring shortening (e.g. Morton's Toe).

A preferred material for the implant is medical grade titanium. However, other medical grade materials can also be used.

Method of Treatment for Abnormal Flexion

As discussed previously, hammer toe malady consists of a combination of dorsifexion of the metatarsal/proximal phalangeal joint 108 (FIG. 1) and plantar flexion of the PIPJ 110 (FIGS. 1, 12A). It is treated by correcting the PIPJ 110 misalignment, as illustrated in FIG. 1 and FIGS. 12A-12E. FIGS. 12A-E illustrate the bones flanking the PIPJ in isolation. This series of figures outline a preferred method of use of the interphalangeal joint implant in which the PIPJ 110 is targeted for correction. In a typical operation, an excision is made to expose an area surrounding the PIPJ 110, the distal end of proximal phalanx 102 and the proximal end of the middle phalanx 104. These bones are then separated, as shown in FIG. 12B, and the articular cartilage on either side of the joint is removed. If the ends of the bones 300, 304 are malformed or damaged the ends of the bones may be osteotomized to create a proper surface for the next step in the procedure as shown in FIG. 12C.

Next, central shafts 302, 306 are introduced into the ends of the bones using standard methods. For example, the ends of the two bones can be "cored" using a trephine, a cylindrical drill with a hollow center. The specifics of the operation are surgeon's choice. For example, to prevent problematic "drift" of the trephine as the teeth first contact the bone, a pilot hole can be drilled first. A trephine with a central drill guide is used as drill guide is inserted into the pilot hole. As long as the drill guide remains in the guide hole, the trephine will remain centered at the proper location during the drilling operation.

After the ends of the bones 300, 304 are cored to form a central channel to the desired depth 302, 306 the two components of the implants 112, 126 are inserted into the bones as shown in FIG. 12D. A proximal phalanx component 112 is designed for insertion into the distal end 300 of the proximal phalanx 102 and a middle phalanx component 126 is designed for insertion into the proximal end 304 of the middle phalanx 104.

The surgeon should drill the channels so that they form a tight fit with the inserts. If there is any doubt the surgeon should err on the side of drilling a channel that is slightly too large. After insertion, tissue ingrowth can, so some extent, fill in and replace the missing bone tissue to produce a lasting phalangeal joint connection.

The distal interphalangeal joint (DIPJ) 111, the joint between the middle phalanx and the distal phalanx, can also be affected by bone misalignment and require stabilization. In this case Kirschner wire (k-wire) is employed. K-wire is directed from within the PIPJ out through the tip of the toe making certain that the proximal end of the wire will not prevent the fastening together of the two implant components. When properly installed, k-wire passes through the center of the implant, the middle phalanx and the distal phalanx. The k-wire typically exits the distal end of the distal phalanx. When installed in this manner, the k-wire in combination with the implant will stabilize the DIPJ 111 as well as the PIPJ 110.

The method functions by restoring a preferred angle, θ, between the central axis of the proximal phalanx and the central axis of the middle phalanx. The angle θ is defined as the degree by which the imaginary central axis of the middle phalanx stem is pointed downward with respect to the imaginary central axis of the proximal phalanx. In one preferred embodiment θ is zero, that is, the two bones are aligned linearly. In another embodiment θ can be any angle between zero and approximately fifteen degrees. In a preferred embodiment θ is approximately ten degrees.

The preferred angles above will be achieved by designing the interphalangeal joint implant so that these same angles are present between the corresponding parts of the implant. The imaginary central axises of the middle phalanx stem and that of the proximal phalanx stem will form the angle θ.

In the specification and claims the expression "approximately" or "generally" are intended to mean at or near, and not exactly, such that the exact location or configuration is not considered critical unless specifically stated.

In the claims in some instances reference has been made to use of the term "means" followed by a statement of function. When that convention is used applicant intends the means to include the specific structural components recited in the specification, including the drawings, and in addition other structures and components that will be recognized by those of skill in the art as equivalent structures for performing the recited function and not merely structural equivalents of the structures as specifically shown and described in the drawings and written specification. The term "attachment" is intended to mean the physical structure disclosed in the specification and also other designs to perform a permanent or reversible connection function such as for example surgical cement, screws, clips, detents, and other attachment structures.

In describing the invention, reference has been made to preferred embodiments. Those skilled in the art however, and familiar with the disclosure of the subject invention, may recognize additions, deletions, substitutions, modifications and/or other changes which will fall within the scope of the invention as defined in the following claims.

What is claimed is:

1. A method of correcting abnormal flexion of a lesser human toe at a proximal interphalangeal joint by fusing a distal end of a proximal phalanx and a proximal end of a corresponding middle phalanx, the method comprising:
    making an incision in an area of a proximal interphalangeal joint;
    separating the bones flanking the proximal interphalangeal joint;
    removing the articular cartilage of the bones flanking the proximal interphalangeal joint;
    drilling a centrally located hole into the distal end of the proximal phalanx;
    drilling a centrally located hole into the proximal end of the middle phalanx;
    inserting into the proximal phalanx hole a proximal phalanx stem which is mounted on a first base plate, said proximal phalanx stem and first base plate comprising a first component;
    inserting into the middle phalanx hole a middle phalanx stem which is mounted on a second base plate, said middle phalanx stem and second base plate comprising a second component;
    after both first and second components are inserted into their respective bones, joining said first and second base plates together with an attachment so that the base plates directly abut thus preventing movement between the base plates in all directions and fixing at a preferred angle said proximal phalanx stem and said middle phalanx stem; and
    closing said incision, wherein said preferred angle is maintained between the proximal phalanx stem and the middle phalanx stem will maintain the proximal phalanx and the middle phalanx bones at the preferred angle thus fusing the proximal phalanx and the middle phalanx bones and thereby correcting abnormal flexion of the proximal interphalangeal joint.

2. A method of correcting abnormal flexion of a lesser human toe as defined in claim 1 wherein said step of joining said base plates together comprises:
    establishing said preferred angle such that an imaginary central axis of the middle phalanx stem is collinear with the imaginary central axis of the proximal phalanx stem.

3. A method of correcting abnormal flexion of a lesser human toe as defined in claim 1 wherein said step of joining said base plates together comprises:
    establishing said preferred angle such that an imaginary central axis of the middle phalanx stem is inclining approximately 10° downward with respect to an imaginary central axis of the proximal phalanx stem and is offset upward with respect to the proximal phalanx stem.

4. A method of correcting improper bone alignment fusing the misaligned bones with an implant,
    said implant comprising a first component and a second component, said first component comprises a first base plate and a first endosseous stem mounted upon said first base plate said second component comprises a second base plate and a second endosseous stem mounted upon said second base plate said first and second components also comprise complementary locking structures configured such that when these complementary locking structures are engaged they securely lock said first base plate directly abutting said second base plate so that a preferred angle is maintained between the longitudinal axis of the first stem and the longitudinal axis of the second stem, said method comprising the steps:

making an incision in an area of a joint between a first bone and a second bone;

separating the bones flanking the joint;

removing the articular cartilage of the bones flanking the joint and exposing ends of the first and seconds bones;

drilling a centrally located hole into the end of the first bone;

drilling a centrally located hole into the end of the second bone;

inserting the first endosseous stem into the first bone, inserting the second endosseous stem into the second bone;

after inserting both first and second endosseous stems into their respective bones, engaging the complementary locking structures to securely lock said first base plate directly to said second base plate, and closing said incision, wherein the preferred angle maintained between the first stem and the second stem causes a preferred angle to be maintained between the first bone and the second bone thus fusing the bones and correcting the improper bone alignment.

5. The method of correcting improper bone alignment as defined in claim 4 wherein said first and second bones are selected from the group consisting of finger and toe bones.

6. The method of correcting improper bone alignment as defined in claim 4 wherein said complementary locking structures include detent arms integrally connected to, and extending from, one component;

said arms are spring loaded when inserted into said other component, opposing apertures are fashioned through said other component; and said arms lock when they reach the apertures in said other component.

* * * * *